(12) United States Patent
Srivatsavayi et al.

(10) Patent No.: US 8,946,479 B2
(45) Date of Patent: Feb. 3, 2015

(54) PROCESS FOR PREPARATION OF 4-FLUORO-α-[2METHYL-L-OXOPROPYL]-γ-OXO—N—β-DIPHENYLBENZENE BUTANE AMIDE

(75) Inventors: Jagapathi Raju Srivatsavayi, Hyderabad (IN); Sairam Pothukuchi, Hyderabad (IN); Srinivasa Sastry Rani, Hyderabad (IN); Mallikarjuna Rao Chikka, Hyderabad (IN); Chiranjeevi Cheekati, Hyderabad (IN); Mallikarjuna Rao Gutti, Hyderabad (IN); Trimurthulu Singavarapu, Hyderabad (IN); Venkat Reddy Thimmaipally, Hyderabad (IN); Venkateswara Rao Tadanki, Hyderabad (IN)

(73) Assignee: Vijayasri Organics Limited, Hyderabad (IN)

( * ) Notice: Subject to any disclaimer, the term of this patent is extended or adjusted under 35 U.S.C. 154(b) by 0 days.

(21) Appl. No.: 13/824,126

(22) PCT Filed: Oct. 13, 2011

(86) PCT No.: PCT/IN2011/000710
§ 371 (c)(1),
(2), (4) Date: Mar. 15, 2013

(87) PCT Pub. No.: WO2012/143933
PCT Pub. Date: Oct. 26, 2012

(65) Prior Publication Data
US 2013/0184493 A1 Jul. 18, 2013

(30) Foreign Application Priority Data
Apr. 21, 2011 (IN) .......................... 1384/CHE/2011

(51) Int. Cl.
C07C 231/12 (2006.01)
C07C 231/22 (2006.01)

(52) U.S. Cl.
CPC ............ *C07C 231/12* (2013.01); *C07C 231/22* (2013.01)
USPC ......................................... 564/169; 564/142

(58) Field of Classification Search
CPC ...................................................... C07C 231/12
USPC ................................................. 564/142, 169
See application file for complete search history.

(56) References Cited

U.S. PATENT DOCUMENTS

2009/0298907 A1  12/2009  Pai et al.

FOREIGN PATENT DOCUMENTS

WO          03/004457          1/2003

OTHER PUBLICATIONS

International Search Report mailed Apr. 20, 2012 for PCT/IN11/00710.

*Primary Examiner* — Shailendra Kumar
(74) *Attorney, Agent, or Firm* — Lowe Hauptman & Ham, LLP

(57) ABSTRACT

A process for preparation of 4-fluoro-α-[2-methyl-1-oxopropyl]-γ-oxo-N-β-diphenylbenzene butane amide also known as a diketone intermediate of atorvastatin, completely devoid of impurities 3,4-difluoro-α-[2-methyl-1-oxopropyl]-γ-oxo-n-β-diphenylbenzene butane amide; methyl, 2{-2[-(4-fluorophenyl)-2-oxo-1-phenylethyl)]}-4-methyl-3-oxo pentanoate; 1,4-bis(4-fluorophenyl)-2,3-diphenylbutane-1,4-dione, 1-(4-fluorophenyl)-2-phenyl ethanone; 1-(4-fluorophenyl)-2-phenyl ethanone and containing about 0.05% or less of 2-methyl-1-oxopropyl]-γ-oxo-N-β-diphenylbenzene butane amide. In that process the said diketone intermediate of formula 1 is obtained by maintaining temperature −25° C. to 50° C. during Friedel-Crafts acylation, in situ halogenation of formula II in presence of a solvent and nucleophilic substitution from a compound of formula III with formula IV in presence of a base.

13 Claims, 9 Drawing Sheets

I

II

III

X= Cl or Br

IV

V

VI

VII

VIII

PROCESS FOR PREPARATION OF 4-FLUORO-α-[2METHYL-L-OXOPROPYL]-γ-OXO—N—β-DIPHENYLBENZENE BUTANE AMIDE

CROSS REFERENCE TO RELATED APPLICATION

This application claims the priority of Indian Patent Application No. 1384/CHE/2011, filed on Apr. 21, 2011 in the Office of the Controller General of Patents, Designs & Trade Marks (CGPDTM). Further, this application is the National Phase application of International Application No. PCT/IN2011/000710, filed Oct. 13, 2011, which designates the United States and was published in English.

FIELD OF THE INVENTION

The invention relates to a process for preparing 4-fluoro-α-[2-methyl-1-oxopropyl]-γ-oxo-N-β-diphenylbenzene butane amide, the diketone intermediate of atorvastatin. More particularly the present invention relates to effective control of impurity formation during the preparation of 4-fluoro-α-[2-methyl-1-oxopropyl]-γ-oxo-n-β-diphenylbenzene butane amide.

BACKGROUND OF THE INVENTION 4-fluoro-α-[2-methyl-1-oxopropyl]-γ-oxo-N-β-diphenylbenzene butane amide, the diketone, is a key intermediary in the preparation of atorvastatin. It had been witnessed that during the preparation of the diketone intermediate of atorvastatin, impurities such as desfluoro and difluoro are also formed. Elimination of the desfluoro diketone impurity poses problems during purification of atorvastain lactone.

WO 2003004457 discloses a new process for preparation diketone of atorvastatin by nucleophilic substitution of 2-bromo-1-(4-fluorophenyl)-2-phenylethanone with 4-methyl-3-oxopentanoic acid anilide in the presence of a base preferably metal hydroxide, carbonate, hydrogen carbonate in suitable solvents like methanol, ethanol, dioxane, tetrahydrofuran, dimethyl formamide, dimethyl acetamide, dimethyl sulfoxide, hexamethylphosphoric acid triamide and the like. This application describes the process of preparation of the above said intermediates from basic raw materials but does not disclose the control of impurities such as desfluoro diketone.

WO 2009/144736 A1 and U.S. Pat. No. 7,872,154 disclose the process for preparation of diketone of atorvastatin by reacting 2-halo-1-(4-fluorophenyl)-2-phenylethanone with 4-methyl-3-oxo-N-phenylpentamide in the presence of base such as sodium carbonate, potassium carbonate, cesium carbonate, diisopropylamine, triethylamine, metal hydroxide, sodium ethoxide, sodium hydride, n-butyl lithium, lithium diisopropylamide in C3-C5 alcohol as solvent. The patents identify the formation of O-alkylated impurity viz., 3-[2-(4-fluorophenyl)-2-oxo-1-phenyl-ethoxy]-4-methyl-pent-2-enoicacid phenylamide during the reaction and describes isolation methods to restrict its presence in diketone to less than 0.1%. The patent also describes the diketone of atorvastatin so obtained contains about 0.1% or less of desfluoro diketone and 0.05% or less of difluoro diketone. However, the patent does not disclose the methods for the preparation of starting materials and only describes that impurities are formed during nucleophilic substitution step.

Accordingly, there is a need for a process of synthesis for preparing 4-fluoro-α-[2-methyl-1-oxopropyl]-γ-oxo-N-β-diphenylbenzene butane amide wherein the impurities formed are either minimized or eliminated.

SUMMARY OF THE INVENTION

According to an aspect of the present invention, provided is a process for controlling impurities formed during the preparation of 4-fluoro-α-[2-methyl-1oxopropyl]-γ-oxo-N-β-diphenylbenzene butane amide comprising the steps of: (I) Friedel-Crafts condensation of fluorobenzene with phenylacetyl chloride at a reaction temperature about −20° C. to 50° C. in presence of Lewis acid catalyst to afford Formula II, (II) Halogenation of said formula II in presence of inert solvents to afford formula III, and (III) Nucleophilic substitution of said formula III in presence of an appropriate base in solvent with formula IV to afford formula I According to another embodiment of the present invention, provided is a process for minimizing formation of impurities during Friedel-Crafts condensation of fluorobenzene with phenylacetyl chloride.

According to another embodiment of the present invention, the Friedel-Crafts condensation is carried out at a reaction temperature about −20° C. to 50° C. and preferably −10° C. to 0° C. in presence of Lewis acid catalyst to afford said Formula II According to another embodiment of the present invention, provided is a process for halogenation of 1-(4-fluorophenyl)-2-phenylethan-1-one to its corresponding 2-halo-1-(4-fluorophenyl)-2-phenylethanone in the presence of methylene chloride as solvent.

According to another embodiment of the present invention, provided is a process for the preparation of 2-halo-1-(4-fluorophenyl)-2-phenylethanone without isolation of intermediary 1-(4-fluorophenyl)-2-phenylethan-1-one.

According to another embodiment of the present invention, provided is a process of Nucleophilic substitution of 2-halo-1(4-fluorophenyl)-2-phenyl ethanone with 4-methyl-3-oxo-N-phenyl pentanamide in the presence of a base in solvent to obtain 4-fluoro-α-[2-methyl-1oxopropyl]-γ-oxo-N-β-diphenylbenzene butane amide.

According to another embodiment of the present invention, provided is a process for controlling impurities formed during the preparation of 4-fluoro-α-[2-methyl-1-oxopropyl]-γ-oxo-N-β-diphenylbenzene butane amide containing about or less of 0.05% of α-[2-methyl-1-oxopropyl]-γ-oxo-N-β-diphenylbenzene butane amide.

According to yet another embodiment of the present invention, provided is a process for controlling impurities formed during the preparation of 4-fluoro-α-[2-methyl-1-oxopropyl]-γ-oxo-N-β-diphenylbenzene butane amide which is completely devoid of 3,4-difluoro-α-[2-methyl-1-oxopropyl]-γ-oxo-n-β-diphenylbenzene butane amide; 1,4-bis(4-fluorophenyl)-2,3-diphenylbutane-1,4-dione; 1-(4-fluorophenyl)-2-phenylethan-1-one and methyl; 2{-2[-(4-fluorophenyl)-2-oxo-1-phenylethyl)]}-4-methyl-3-oxo pentanoate.

According to yet another embodiment of the present invention, provided is an analytical method to detect impurities in the preparation 4-fluoro-α-[2-methyl-1oxopropyl]-γ-oxo-N-β-diphenylbenzene butane amide by ultra performance liquid chromatography (UPLC).

BRIEF DESCRIPTION OF DRAWINGS

The advantages and features of the present invention will become better understood with reference to the following detailed description with the accompanying figures, wherein like elements are identified with like symbols, and in which.

DETAILED DESCRIPTION

The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present invention.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

Figure 1:
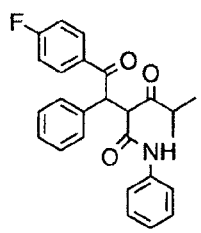
FIG. 1 illustrates structural formula of compounds
Figure 1:
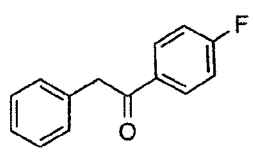
Figure 1:
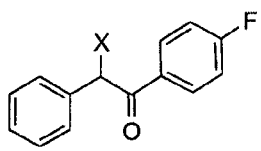
Figure 1:
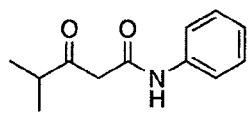
Figure 1:
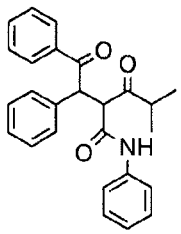
Figure 1:
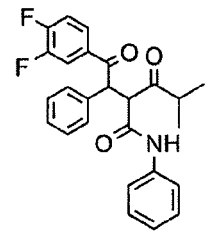
Figure 1:
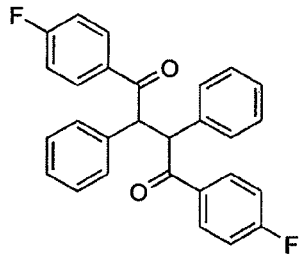
Figure 1:
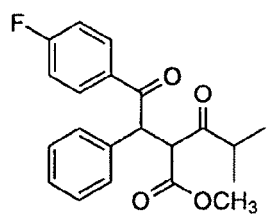

FIG. 1 illustrates the details of the compounds used in the present invention. The compounds includes;
4-fluoro-α-[2-methyl-1-oxopropyl]-γ-oxo-N-β-diphenyl-benzene butane amide as Formula I;
1-(4-fluorophenyl)-2-phenylethan-1-one as Formula II;
2-halo-1-(4-fluorophenyl)-2-phenylethan-1-one as Formula III;
4-methyl-3-oxo-N-phenyl pentanamide as Formula IV;
α-[2-methyl-1-oxopropyl]-γ-oxo-N-β-diphenylbenzene butane amide as Formula V;
3,4-difluoro-α-[2-methyl-1-oxopropyl]-γ-oxo-n-β-diphenylbenzene butane amide as Formula VI;
1,4-bis(4-fluorophenyl)-2,3-diphenylbutane-1,4-dione as Formula VII and methyl, 2{-2[(4-fluorophenyl)-2-oxo-1-phenylethyl)]}-4-methyl-3-oxo pentanoate as Formula VIII.

Figure 2:
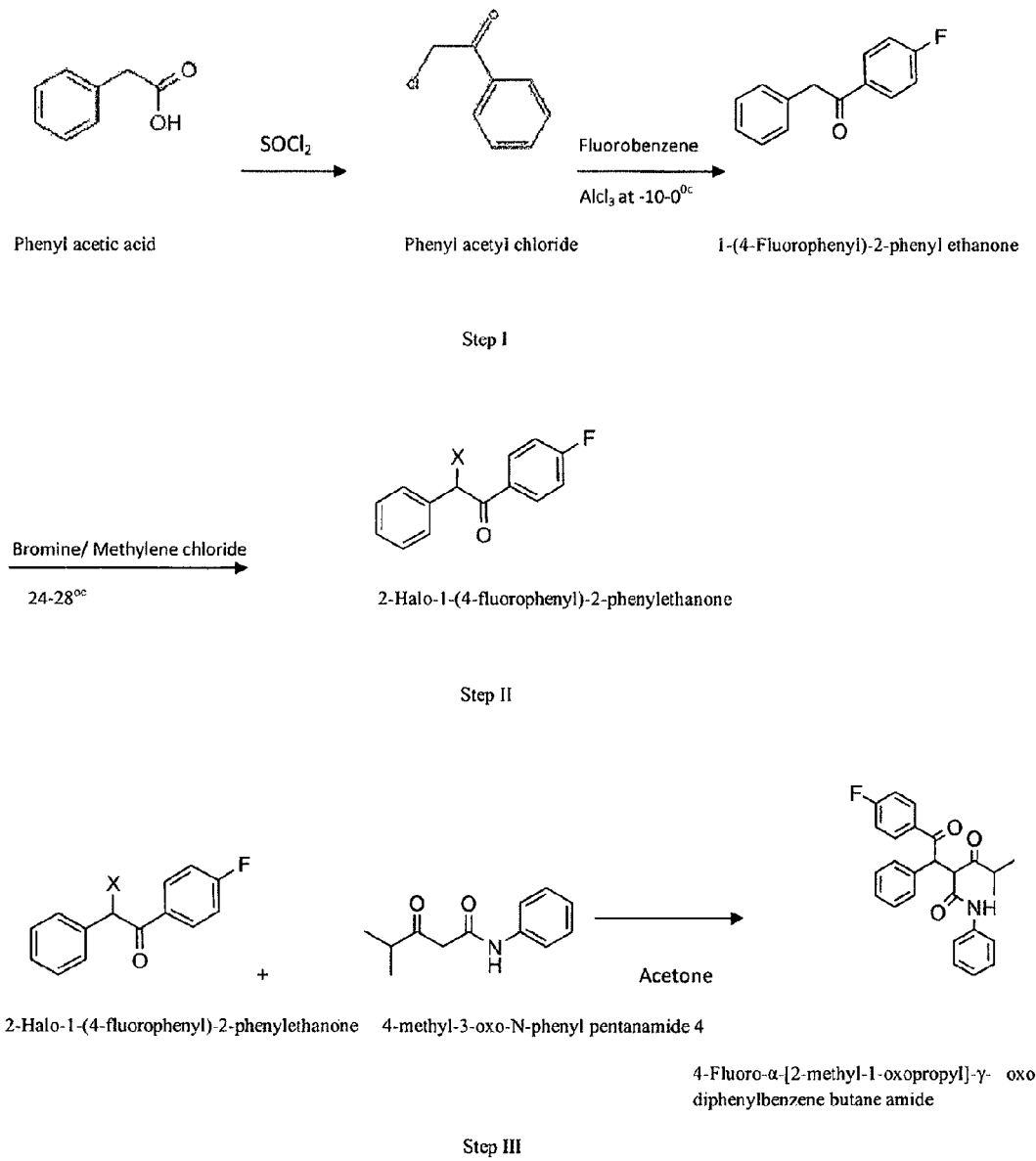
FIG. 2 illustrates route of synthesis for preparation of 4-fluoro-α-[2-methyl-1-oxopropyl]-γ-oxo-N-β-diphenyl-benzene butane amide.

FIG. 2 illustrates route of synthesis for preparation of diketone of atorvastatin. As illustrated it comprises the following steps Step I:
Friedel-Crafts condensation of fluorobenzene with phenyl acetyl chloride gives rise to 1-(4-fluorophenyl)-2-phenyl ethanone;

Step II:
Halogenation of 1-(4-fluorophenyl)-2-phenyl ethanone in presence of inert solvents gives rise to 2-halo-1(4-fluorophenyl)-2-phenylethanone; and Step III:
Nucleophilic substitution of 2-halo-1(4-fluorophenyl)-2-phenylethanone with 4-methyl-3-oxo-N-phenyl pentanamide in presence of an appropriate base in solvent gives rise to diketone of atorvastatin Normally fluorobenzene of commercial grade often contains benzene up to 300 ppm and trace amounts of difluorobenzene as contaminants, which on reacting with phenyl acetyl chloride under conventional Friedel-Crafts acylation procedures would give rise to their corresponding acetylated derivatives, 1,2-diphenyl ethanone (deoxy benzoin) and 1-(3,4-difluorophenyl)-2-phenyl ethanone, respectively.

These impurities once formed are difficult to remove from desired product by routine crystallization procedures as their solubility index is similar that of 1-(4-fluorophenyl)-2-phenylethanone. Furthermore these impurities are functionally similar to 1-(4-fluorophenyl)-2-phenyl ethanone and would undergo chemical transformations in similar way in the subsequent reaction steps.

According to present invention, Friedel-Crafts condensation of fluorobenzene with phenyl acetyl chloride is carried out in the presence of Lewis acid catalyst such as $AlCl_3$, $FeCl_3$, $SbCl_5$, $BF_3$, $TiCl_4$ or $ZnCl_2$. The condensation is carried out preferably in the absence of solvents or in the presence of halogenated hydrocarbons such as methylene chloride. The mole ratio of phenyl acetyl chloride and Lewis acid catalyst ranges from 0.75 to 1.5 and, preferably 1.08 by maintaining temperatures ranging from −20° C. to 50° C., −15° to +5° C., preferably at −10° C. to 0° C. for 6-12 hours, preferably for 6 hours. The condensation is monitored by TLC/HPLC using methylene chloride as solvent to afford 1-(4-fluorophenyl)-2-phenyl ethanone in substantially pure form, and can be purified further by crystallization from n-hexane.

According to step II of the present invention, halogenation of 1-(4-fluorophenyl)-2-phenyl ethanone is carried out at α-carbon by treating 1-(4-fluorophenyl)-2-phenyl ethanone with either sulphuryl chloride/chlorine gas or elemental bromine in the presence of hydrogen bromide in acetic acid to afford 2-halo-1(4-fluorophenyl)-2-phenyl ethanone. The halogen atom can be bromine or chlorine, preferably chlorine.

The halogenation reaction is carried out preferably in an inert solvent especially methylene chloride. The reaction temperature is about 20 to 50° C., especially between 25 to 30° C., The halogenation reaction can be accomplished in the manner described above on crystallized form of 1-(4-fluorophenyl)-2-phenyl ethanone or a methylene chloride solution obtained from Friedel-Crafts condensation of fluorobenzene and phenyl acetyl chloride.

According to step III of the present invention, Nucleophilic substitution of 2-halo-1(4-fluorophenyl)-2-phenylethanone with 4-methyl-3-oxo-N-phenyl pentanamide is carried out in presence of a base in a solvent. The base may be inorganic salts like sodium carbonate, potassium carbonate, cesium carbonate their hydrogen carbonates/alkoxides or organic bases such as triethyl amine, diisopropylethylamine etc. The nucleophilic substitution is accomplished in solvents such as tetrahydrofuran, 1,2-dimethoxy ethane, methylene chloride, ethyl acetate, acetone, methyl ethyl ketone, methyl isobutyl ketone, isopropanol, acetonitrile, dimethyl formamide, N-methyl pyyrolidinone, dimethyl sulfoxide and methanol or a mixture there of.

Further, higher yields of 4-fluoro-α-[2-methyl-1oxopropyl]-γ-oxo-N-β-diphenylbenzene butane amide can be obtained by adding a mixture of 2-halo-1(4-fluorophenyl)-2-phenyl ethanone with 4-methyl-3-oxo-N-phenyl pentanamide to a slurry of potassium carbonate in acetone 18-20° C.

The effect of the solvent during nucleophilic substitution of 2-halo-1(4-fluorophenyl)-2-phenyl ethanone by the anion of 4-methyl-3-oxo-N-phenyl pentanamide is studied with respect to impurity generation. It is observed that formation of 1(4-fluorophenyl)-2-phenylethanone is more than 15%, when less polar solvents like tetrahydrofuran, 1,2-dimethoxy ethane, methylene chloride and ethyl acetate are used as solvent for the reaction. Although more polar solvents like acetonitrile, N,N-dimethyl formamide, n-methyl pyrrolidone, dimethyl sulfoxide and methanol that have tendency to capture the proton released from 4-methyl-3-oxo-N-phenyl pentanamide during anion generation, when used as solvent for the nucleophilic substitution, resulted in the formation of 1(4-fluorophenyl)-2-phenylethanone to about 3-6%.

The effect of solvents is summarized in the following table:

| S. No | Solvent | Rxn Temp 0° C. | Rxn Hrs | HPLC (area %) of reaction mixture | | | | | | Purity of I after isolation | I Yield % |
|---|---|---|---|---|---|---|---|---|---|---|---|
| | | | | II | V | Isomer of I | I | VIII | VII | | |
| 1 | THF | 25-30 | 6 | 20.52 | 1.88 | 7.03 | 44.54 | 1.19 | 0.09 | 99.40 | 32.0 |
| 2 | DME | 25-30 | 3 | 18.73 | 1.31 | 7.46 | 52.78 | 0.62 | 0.07 | 99.62 | 36.9 |
| 3 | MDC | 25-30 | 20 | 22.68 | 1.38 | 6.36 | 37.2 | 0.29 | 0.05 | 98.3 | 21.1 |
| 4 | EtAc | 25-30 | 6 | 17.36 | 0.21 | 0.76 | 66.31 | 1.11 | 0.36 | 99.44 | 49.3 |
| 5 | Acetone | 25-30 | 3 | 7.43 | 0.27 | 0.54 | 83.36 | 0.32 | 0.17 | 99.47 | 73.8 |
| 6 | MEK | 25-30 | 3 | 8.13 | 0.21 | 0.90 | 81.97 | 0.48 | — | 99.70 | 68.0 |
| 7 | MIBK | 25-30 | 3 | 10.37 | 0.97 | 3.34 | 71.04 | 0.52 | 0.12 | 99.05 | 55.4 |
| 8 | IPA | 25-30 | 7 | 4.82 | 0.47 | 1.44 | 85.52 | 0.38 | 0.08 | 99.43 | 73.2 |
| 9 | ACN | 25-30 | 4 | 6.15 | 2.13 | 7.26 | 68.43 | 0.25 | 0.28 | 99.44 | 61.6 |
| 10 | DMF | 25-30 | 4 | 2.30 | 2.12 | 6.50 | 52.02 | 0.32 | 0.22 | 94.12 | 24.6 |
| 11 | NMP | 25-30 | 3 | 2.78 | 2.42 | 8.68 | 71.26 | 0.28 | 0.10 | 90.64 | 49.3 |
| 12 | DMSO | 25-30 | 4 | 0.91 | 6.07 | 5.12 | 53.84 | 1.04 | 0.31 | — | — |
| 13 | Methanol | 25-30 | 7 | 10.41 | 1.44 | 6.23 | 42.05 | 0.35 | 0.18 | 98.48 | 39.4 |

THF = Tetrahydrofuran,
DME = 1,2-Dimethoxyethane,
MDC = Methylene chloride,
ETAc = Ethylacetate,
MEK = Methylethylketone,
IBK = Methylisobutylketone,
IPA = Isopropylalcohol,
ACN = Acetonitrile,
DMF = Dimethylformamide,
NMP = N-Methylpyrrolidone,
DMSO = Dimethylsulfoxide.

Reactions are conducted using stoichiometry of raw materials given under examples. HPLC of reaction mixture and isolated product (I) is performed on Zorbax SB C18, 150 mm×4.6 mm, 3.5 microns, flow rate 1.2 ml/min, run time 50 min.

As per the above table, acetone, methyl ethyl ketone and isopropanol are best suited as solvent for carrying out nuleophilic substitution of 2-halo-1(4-fluorophenyl)-2-phenyl ethanone with 4-methyl-3-oxo-N-phenyl pentanamide due to lesser formation of impurities.

It is also observed that in step III, impurities are formed during nucleophilic substitution reaction. One of the impurities formed during the nucleophilic substitution reaction of 2-halo-1(4-fluorophenyl)-2-phenylethanone with 4-methyl-3-oxo-N-phenyl pentanamide is formation of 1-(4-fluorophenyl)-2-phenyl ethanone (II), possibly formed by electrophilic attack (here in, H$^+$ ion released from 4-methyl-3-oxo-N-phenyl pentanamide during its anion generation) on 2-halo-1(4-fluorophenyl)-2-phenylethanone. The formation of 1-(4-fluorophenyl)-2-phenyl ethanone (II), is studied by HPLC and UPLC methods, and it is observed that the aforesaid impurity can be formed up to 6-8% during reaction.

Furthermore, 1-(4-fluorophenyl)-2-phenyl ethanone thus generated in situ can give rise to its corresponding anion in the presence of base like potassium carbonate and undergoes reaction with 2-halo-1(4-fluorophenyl)-2-phenylethanone giving rise to another impurity 1,4-bis(4-fluorophenyl)-2,3-diphenylbutane-1,4-dione (VII) which can be isolated by using chromatographic techniques.

Figure 3:
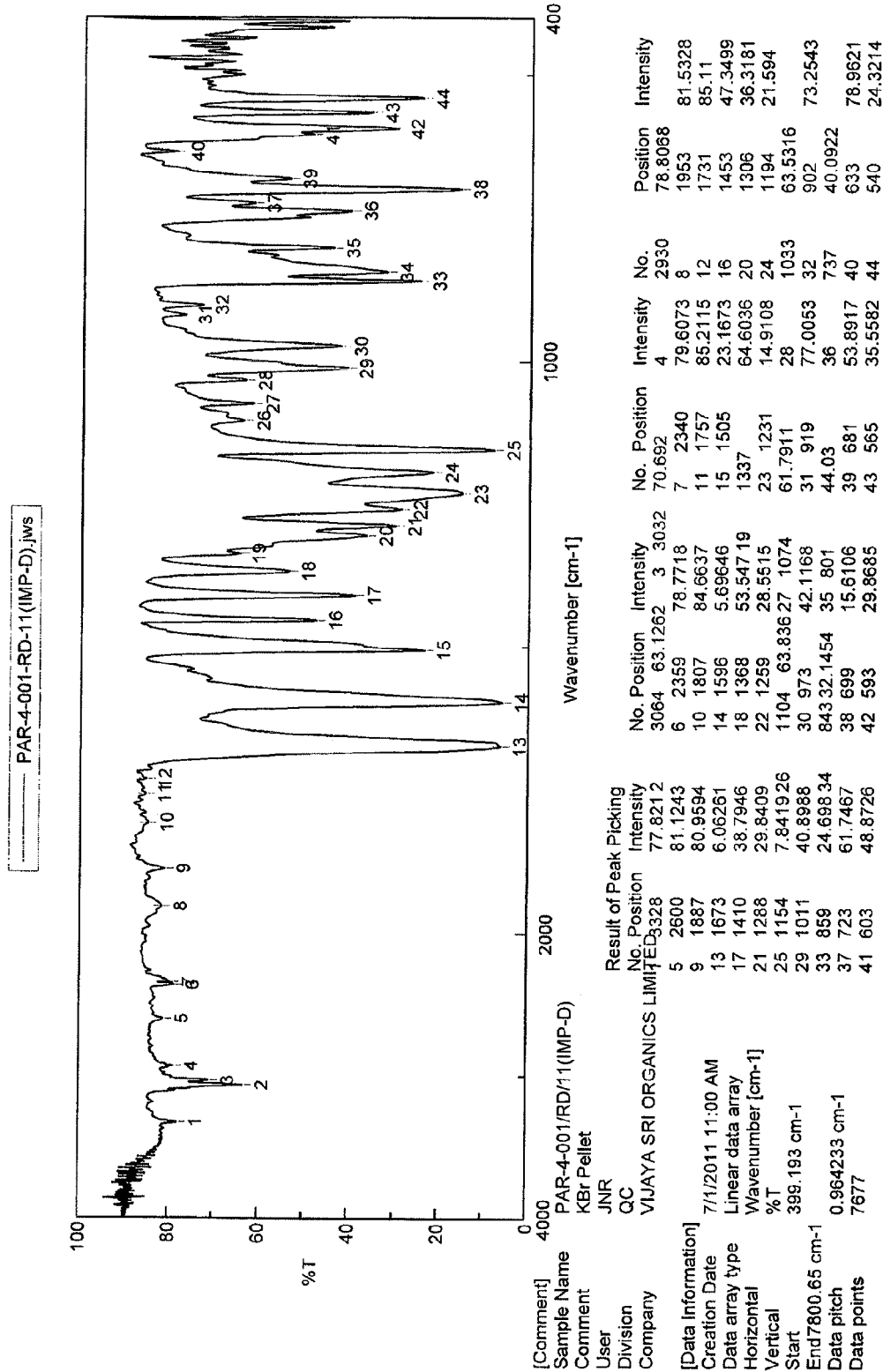
FIG. 3 illustrates IR spectrum of 1,4-bis(4-fluorophenyl)-2,3-diphenylbutane-1,4-dione.
Figure 4:
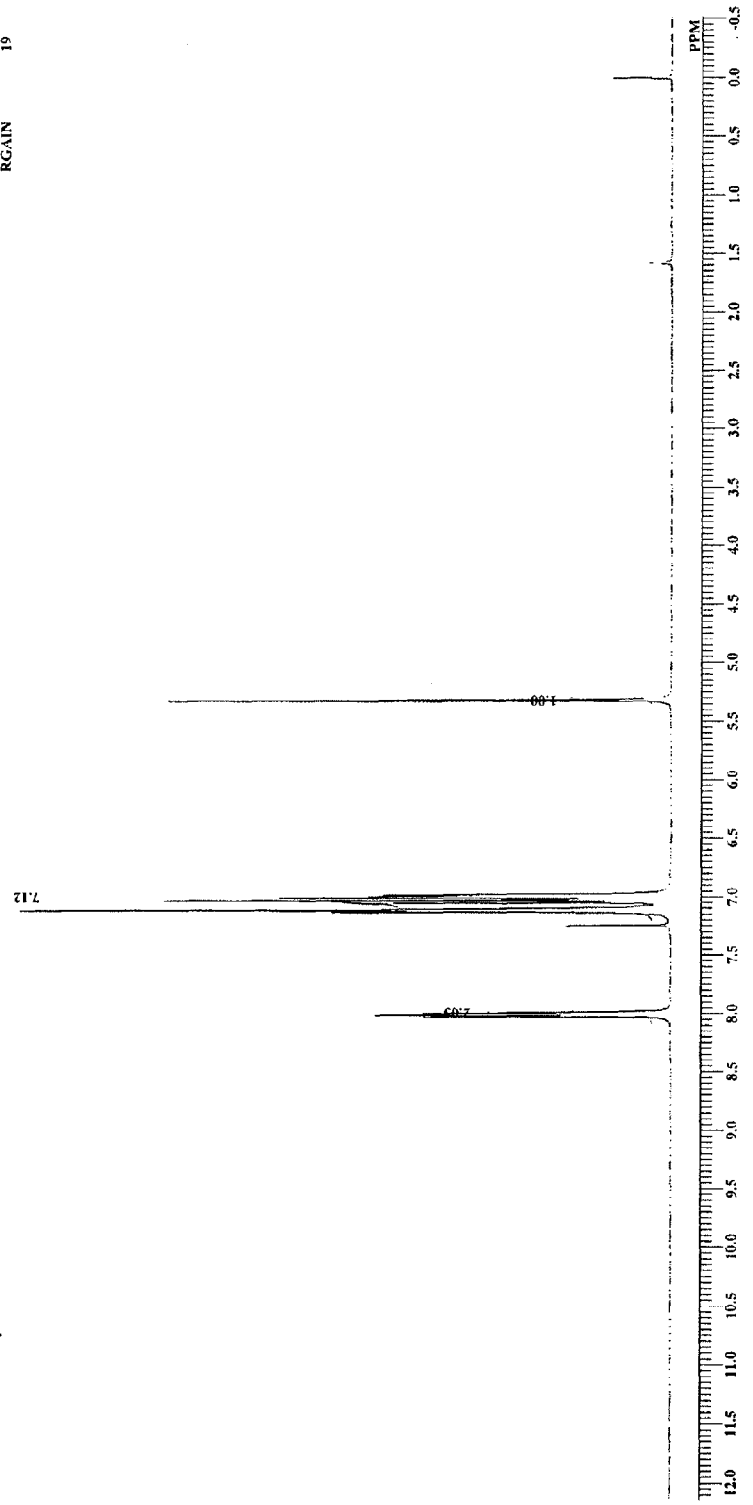
FIG. 4 illustrates $^1$H NMR of 1,4-bis(4-fluorophenyl)-2,3-diphenylbutane-1,4-dione.
Figure 5:
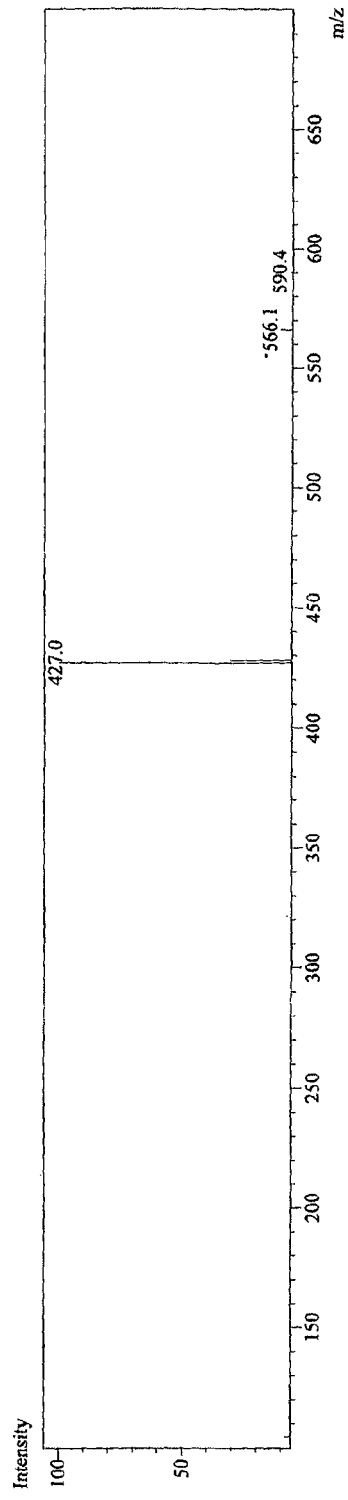
FIG. 5 illustrates Mass spectrum of 1,4-bis(4-fluorophenyl)-2,3-diphenylbutane-1,4-dione.
Figure 5:
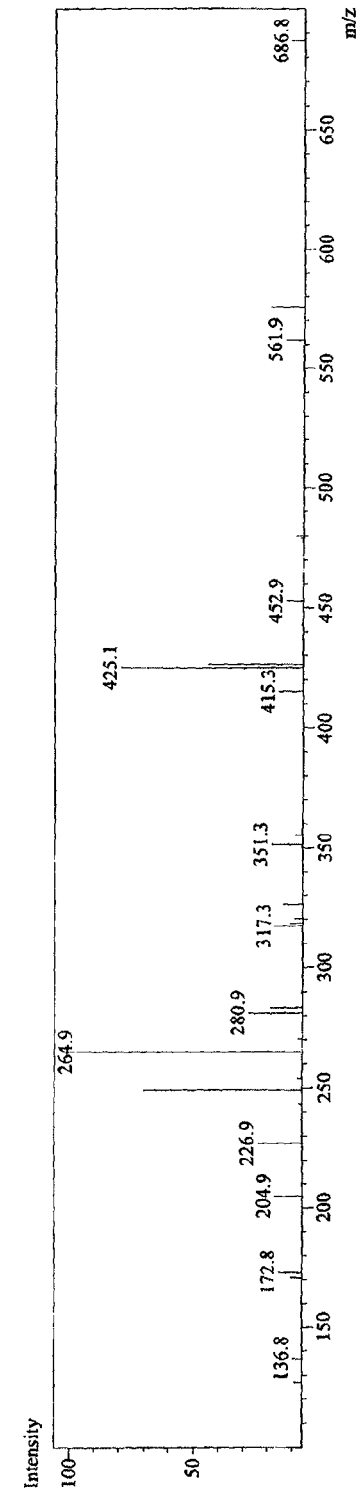

1,4-bis(4-fluorophenyl)-2,3-diphenylbutane-1,4-dione thus isolated by preparative HPLC technique followed by crystallization, has been characterized by IR, NMR and Mass spectral data. As depicted in FIG. 3, the IR spectrum showed absorbance at 1673 cm$^{-1}$ (carbonyl stretching of γ diketone), 1596 cm$^{-1}$ (C=C aromatic stretching) and 1154 cm$^{-1}$ (for C—F stretching). As depicted in FIG. 4, $^1$H NMR (400 MHz, CDCl$_3$) showed methane protons at 5.3(2H, s), aromatic protons between 7.0-8.0 (14H, m). Further as depicted in FIG. 5, Mass spectroscopy of VII showed molecular ions at 427, 425, 351, 317, 280, 264, 250, 226, 204, 172 and 134.

Another impurity formed in the preparation of 4-fluoro-α-[2-methyl-1-oxopropyl]-γ-oxo-N-β-diphenylbenzene butane amide is methyl, 2{-2[-(4-fluorophenyl)-2-oxo-1-phenylethyl)]}-4-methyl-3-oxo pentanoate. This impurity originates from 4-Methyl-3-oxo-N-phenyl pentanamide, often prepared in situ by reaction of methyl isobutyryl acetate and aniline prior to nulceophilic substitution of 2-bromo-1(4-fluorophenyl)-2-phenyl ethanone. It is observed in some situations, unreacted methyl isobutyryl acetate if unchecked for its presence, itself reacts with 2-bromo-1(4-fluorophenyl)-2-phenyl ethanone, giving methyl, 2{-2[-4-(4-fluorophenyl)-2-oxo-1-phenylethyl)]}-4-methyl-3-oxo pentanoate (VIII). This impurity is isolated from the mixture by using column chromatography techniques followed by crystallization.

Figure 6:
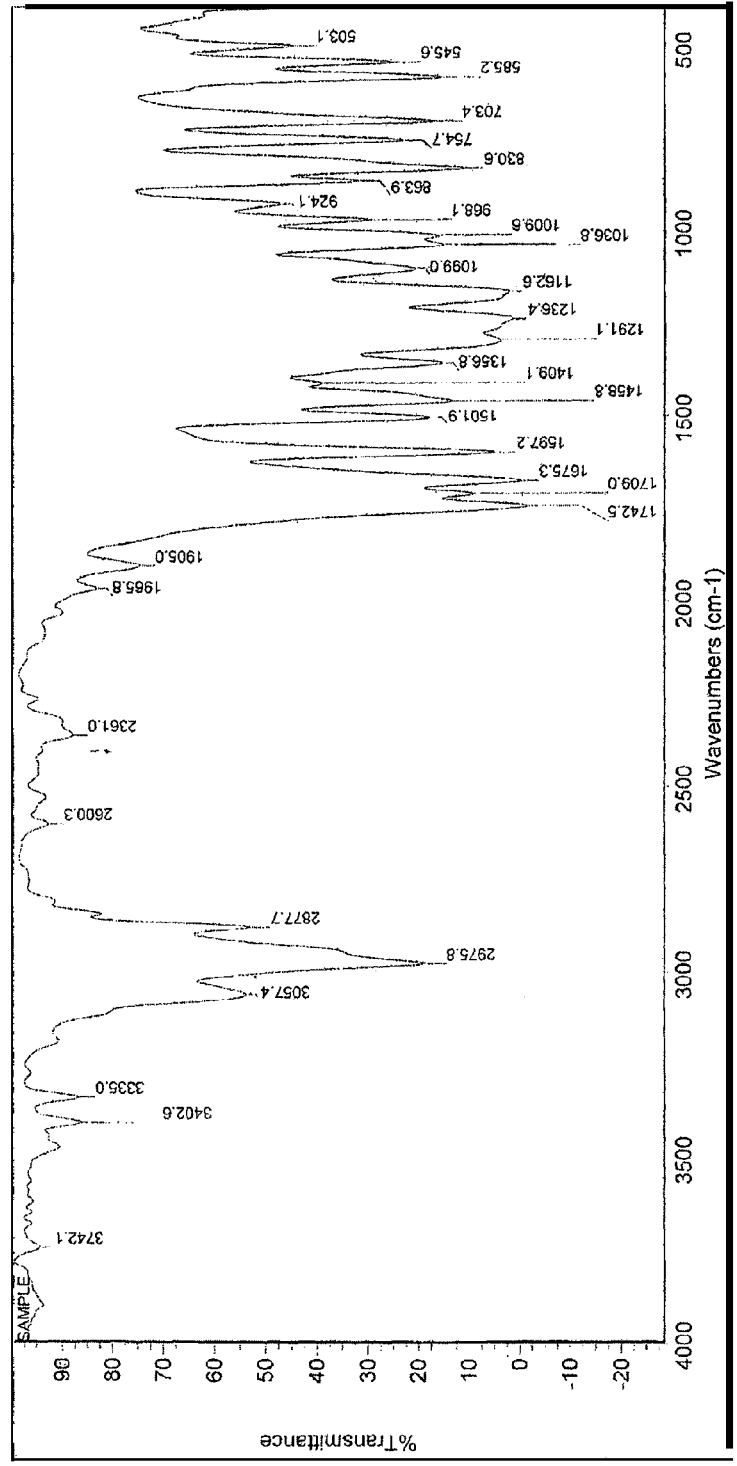
FIG. 6 illustrates IR spectrum of methyl,2{-2[-(4-fluorophenyl)-2-oxo-1-phenylethyl)]}-4-methyl-3-oxo pentanoate.
Figure 7:
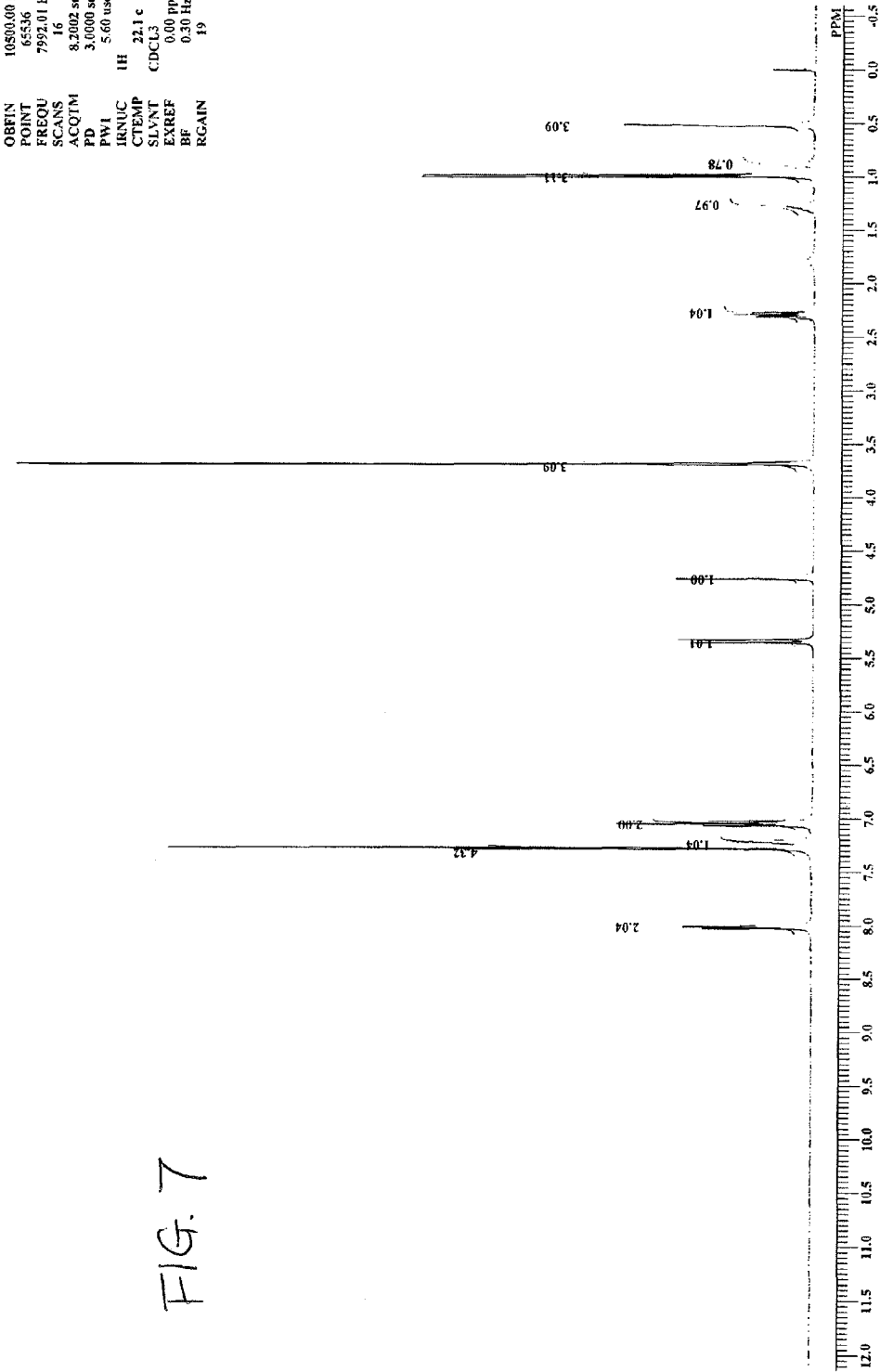
FIG. 7 illustrates $^1$H NMR of methyl,2{-2[-(4-fluorophenyl)-2-oxo-1-phenylethyl)]}-4-methyl-3-oxo pentanoate.

The aforesaid compound is characterized by IR, $^1$HNMR and Mass spectra. As depicted in FIG. 6, the IR spectrum showed absorbance at 1675 cm$^{-1}$ (carbonyl stretching of γ diketone), 1724 cm$^{-1}$ (Carbonyl stretching of ester group) and 1162 cm$^{-1}$ (for C—O—C stretching). Further as depicted in FIG. 7, $^1$HNMR (400 MHz, CDCl$_3$) showed methyl protons at 0.5 (3H,d) and 1.0 (3H,d), methine(alkyl) proton at 2.3(1H,m), O—CH$_3$ at 3.7 (3H,s), methine (benzylic) at 4.75

Figure 8:
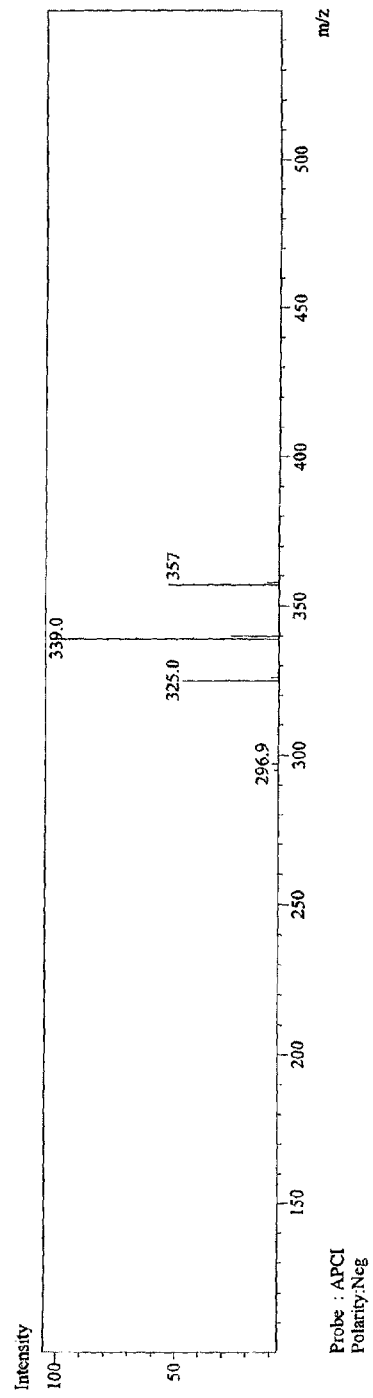
FIG. 8 illustrates Mass spectrum of methyl, 2{-2[-(4-fluorophenyl)-2-oxo-1-phenylethyl)]}-4-methyl-3-oxo pentanoate
Figure 8:
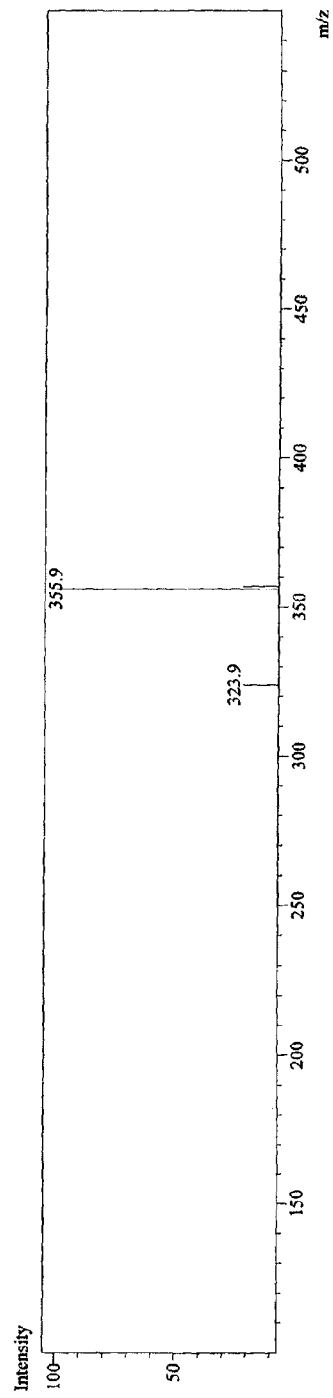

(1H,d) and 5.35 (1H, d), aromatic protons at 7.0 to 8.0 (9H, m). Further as depicted in FIG. 8 Mass spectrum showed molecular ion at 356.9, 355.9 and 323.8. The retention time and relative retention time of 2 {-2 [-(4-fluorophenyl)-2-oxo-1-phenylethyl)]}-4-methyl-3-oxo pentanoate (VIII) with respect to 4-fluoro-α-[2-methyl-1-oxopropyl]-γ-oxo-N-β-diphenylbenzene butane amide is determined by UPLC and HPLC technique.

Figure 9:
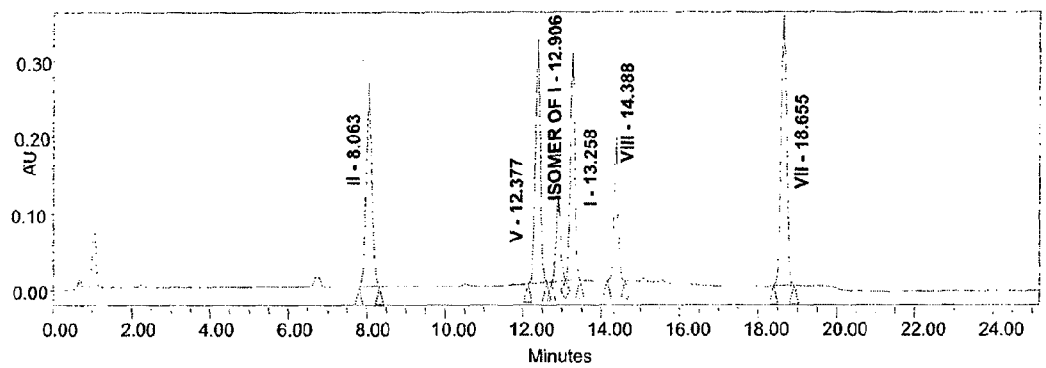
FIG. 9 illustrates Ultra performance liquid chromatography (UPLC) of the impurities.

As depicted in FIG. 9, Ultra performance liquid chromatography (UPLC) method has been used for detection and quantification of 1-(4-fluorophenyl)-2-phenyl ethanone (II), α-[2-methyl-1-oxopropyl]-γ-oxo-N-β-diphenylbenzene butane amide (V), 4-fluoro-α-[2-methyl-1-oxopropyl]-γ-oxo-N-β-diphenylbenzene butane amide (VII), difluoro ketone of formula VI and probable impurity such as methyl, 2{-2[-(4-fluorophenyl)-2-oxo-1-phenylethyl)]}-4-methyl-3-oxo pentanoate (VIII).

UPLC takes advantage of small 1.7 μm particles operated at elevated pressures to achieve un-compromisable separation speed resolution, and sensitivity. The UPLC system allows shortening analysis time comparing to the conventional system using 5 μm particle packed analytical columns. In comparison with 2-5 μm particle packed analytical column analysis should be shortened significantly. The negative effect of particles decrease by increasing backpressure, The Separation on UPLC is performed under very high pressure (up to 100 Mpa is possible in UPLC system), but it has no negative influence on analytical column or other components of chromatographic system. Separation efficiency remains maintained and even improved.

For separation of impurities in 4-fluoro-α-[2-methyl-1-oxopropyl]-γ-oxo-N-β-diphenylbenzene butane amide using waters Acquity UPLC system adopted gradient mobile phase of phosphate buffer and acetonitrile in the ratio of initial concentration as 70:30 on 100 mm length column with 2 micron particle size at a flow rate of 0.3 ml/min.

EXAMPLE-1

1-(4-Fluorophenyl)-2-phenyl ethanone (II)

Fluorobenzene (100 g, 1.04 mol) is taken in a clean and dry 4 necked RB flask equipped with mechanical stirring rod, pressure equalization funnel, $N_2$ inlet and a $CaCl_2$ guard tube. The contents of the flask are cooled to 0° C. in an ice bath under a stream of $N_2$ gas. 103 g (0.768 mol) of powdered aluminum chloride are added into the flask under stirring. The contents of the flask are further cooled to −10° C. by adding common salt to ice bath. Phenyl acetyl chloride (110.75 g, 0.717 moles) is placed in the pressure equalization funnel fitted to the flask and added drop wise manner in 2-2½ hours, while maintaining the temperature of the reaction between −10° to 0° C. After the addition the reaction is maintained for a further period of 2 hours between −10° to 0° C. In process sample of reaction mixture showed the area % of 1-(4-Fluorophenyl)-2-phenyl ethanone by HPLC as 98.55%. The reaction mixture is then poured slowly into a mixture of ice (300 g), water (300 ml) and Conc.hydrochloric acid (30 ml) while maintain the temperature between −10 to 5° C. the contents are stirred for ½ hr at this temperature. The solid thus obtained is washed successively with water (2×200 ml) and is transferred into RB flask. The wet solid is dissolved in 250 ml of Petroleum Ether (60-80° C.) at 62.5±2.5° C. The contents are cooled to 30° C., and water thus separated from organic phase is removed. The organic phase is cooled to 18±2° C. under stirring and maintained for additional 1 hr at 18±2° C. The product is isolated on a filter and washed with cold Petrolueum Ether(25 ml) and dried at 42.5±2.5° C. till water content is <0.5%. Yield 122 g (77.7%)

| Peak | UPLC | | | HPLC | | |
|---|---|---|---|---|---|---|
| | RT | RRT | Area (%) | RT | RRT | Area (%) |
| 1-(4-Fluorophenyl)-2-phenyl ethanone (II) | 8.06 | 1.0 | 99.47 | 7.405 | 1.0 | 99.17 |
| Deoxy benzoin | 7.229 | 0.903 | nil | 6.710 | 0.905 | nil |

EXAMPLE-2

2-Bromo-1-(4-fluorophenyl)-2-phenylethanone

Methylene chloride (1 L) is taken in a 4 necked RB flask equipped with mechanical strring rod, pressure equalization funnel and a $CaCl_2$ guard tube. 100 g (0.466 mol) of 1-(4-Fluorophenyl)-2-phenyl ethanone is introduced in to the above flask and stirred for 5 minutes to obtain a clear solution.2 ml of a 30% hydrobromic acid in acetic acid is then added, followed by gradual addition of a cold solution of bromine (73 g, 0.456 mole) in 200 ml of methylene chloride at 26±2° C. Bromine solution is added in such a manner that it is consumed instantly as indicated by colouration of reaction mixture. After addition of bromine solution the reaction mixture is cooled to 19±1° C., treated with 5% aqueous sodium sulphite (200 ml) and stirred for about 1hr at 21.5±3.5° C. The organic layer is then separated and is subjected to the above operation twice with 5% aqueous sodium sulphite (2×200 ml). The organic layer is then stirred with 5% aqueous sodium bicarbonate (200 ml) for about 1 hr at 21.5±3.5° C. and separated. The organic layer is finally stirred with 5% aqueous sodium chloride(200 ml) and separated. The organic layer is dried over sodium sulphate and filtered. Methylene chloride is removed by distillation and the syrup thus obtained solidified on standing in to a pale orange coloured solid. Yield 129 g (94.8%)

| Peak | UPLC | | | HPLC | | |
|---|---|---|---|---|---|---|
| | RT | RRT | Area (%) | RT | RRT | Area (%) |
| 2-Bromo-1-(4-fluorophenyl)-2-phenyl ethanone | 11.705 | 1.0 | 97.63 | 7.096 | 1.0 | 98.31 |
| 2-Bromo-1,2-diphenyl ethanone | 10.46 | 0.893 | 0.05 | 6.576 | 0.927 | Nil |

EXAMPLE-3

4-Fluoro-α-[2-methyl-1-oxopropyl]-γ-oxo-N-β-diphenylbenzene butane amide

Acetone (320 ml) is taken in a 4 necked RB flask equipped with mechanical stirring rod, pressure equalization funnel and a $CaCl_2$ guard tube. 100 g (0.487 mol) of 4-methyl-3-oxo-N-phenyl pentanamide is added and stirred for 5 min to obtain clear solution. The solution is then cooled to 18.5±1.5° C. and 80 g (0.579 mole) of potassium carbonate is introduced in one lot. A solution of 114 g (0.389 mol) of 2-Bromo-1-(4-fluorophenyl)-2-phenylethanone in acetone (120 ml) is added to contents of flask in about 1½-2 hr period while maintaining the reaction temperature at 18.5±1.5° C. After addition the reaction mixture temperature is raised to 26±2° C. and maintained for additional 6 hours. The reaction mixture is filtered and the inorganics are washed with acetone (100 ml). The combined filtrate is concentrated to residual solid by removing acetone below 65° C. under vacuum. 32 ml of isopropyl alcohol is then added to the flask and solvent is removed completely under vacuum below 70° C. Again 32 ml of fresh isopropyl alcohol is added to residue and solvent is removed completely under vacuum below 70° C. 320 ml of isopropyl alcohol is added to the residual solid and the contents are heated to 82.5±2.5 and maintained at this temperature for 1 hour. The contents are gradually brought to 32±2.5° C. by cooling during a period of 1½-2 hours. The product is isolated on filter and washed with 32 ml of isopropyl alcohol and followed by water (200 ml). The material is dried at 75±5° C. in a vacuum oven, till water content of material is <0.5%. Yield 120 g (73.8%)

| | | UPLC | | | HPLC | |
|---|---|---|---|---|---|---|
| Peak | RT | RRT | Area (%) | RT | RRT | Area (%) |
| 4-Fluoro-α-[2-methyl-1-oxopropyl]-γ-oxo-N-β-diphenylbenzene butane amide | 13.25 | 1.0 | 99.75 | 25.112 | 1.0 | 99.50 |
| 1-(4-Fluorophenyl)-2-phenyl ethanone (II) | 8.063 | 0.608 | nil | 13.144 | 0.522 | 0.01 |
| Desfluoro analog | 12.377 | 0.934 | nil | 23.008 | 0.916 | 0.007 |
| Difluoro analog | 14.30 | 1.079 | nil | 27.502 | 1.091 | nil |
| Isomer | 12.90 | 0.980 | Nil | 22.40 | 0.960 | 0.029 |
| Compound VIII | 14.38 | 1.085 | nil | 27.507 | 1.096 | nil |
| Compound VII | 18.65 | 1.407 | nil | 35.462 | 1.414 | nil |

EXAMPLE-4

2-Bromo-1-(4-fluorophenyl)-2-phenylethanone

Fluorobenzene (100 g, 1.04 mol) is taken in a clean and dry 4 necked RB flask equipped with mechanical stirring rod, pressure equalization funnel, $N_2$ inlet and a $CaCl_2$ guard tube. The contents of the flask are cooled to 0° C. in an ice bath under a stream of $N_2$ gas. 103 g (1.54 mol) of powdered aluminum chloride are added into the flask under stirring. The contents of the flask are further cooled to –10° C. by adding common salt to ice bath. Phenyl acetyl chloride (110.75 g, 1.43 mol) is placed in the pressure equalization funnel fitted to the flask and added drop wise manner in 2-2½ hours, while maintaining the temperature of the reaction between –10° to 0° C. After the addition the reaction is maintained for a further period of 2 hours between –10° to 0° C. In process sample of reaction mixture showed the area % of 1-(4-Fluorophenyl)-2-phenyl ethanone by HPLC as 99.02% and deoxy benzoin content as nil. The reaction mixture is then poured slowly into a mixture of ice (300 g), water (300 ml) and Conc.hydrochloric acid (30 ml) while maintain the temperature between –10 to 5° C. the contents are stirred for ½ hr at this temperature. The solid thus obtained is dissolved in methylene chloride (1.0 L) and separated the organic phase. The aqueous phase is extracted with methylene chloride (500 ml).The combined methylene chloride extract is sequentially washed with 5% aqueous sodium bicarbonate (600 ml), water (600 ml) and 5% sodium chloride (400 ml). The methylene chloride extract is then transferred into a 4 necked RB flask equipped with mechanical strring rod, pressure equalization funnel and a $CaCl_2$ guard tube. 4 ml of a 30% hydrobromic acid in acetic acid is then added, followed by gradual addition of a cold solution of bromine 109 g, 0.68 mole) in 200 ml of methylene chloride at 26±2° C. Bromine solution is added in such a manner that it is consumed instantly as indicated by colouration of reaction mixture. After addition of bromine solution the reaction mixture is cooled to 19±1° C., treated with 5% aqueous sodium sulphite (400 ml) and stirred for about 1hr at 21.5±3.5° C. The organic layer is then separated and is subjected to the above operation twice with 5% aqueous sodium sulphite (2×400 ml). The organic layer is stirred with 5% aqueous sodium bicarbonate (400 ml) for about 1 hr at 21.5±3.5° C. and separated. The organic layer is finally stirred with 5% aqueous sodium chloride(400 ml) and separated. The organic layer is dried over sodium sulphate and filtered. Methylene chloride is removed by distillation and the syrup thus obtained solidified on standing in to a pale orange coloured solid. Yield 183 g (85.9%)

| | | UPLC | | | HPLC | |
|---|---|---|---|---|---|---|
| Peak | RT | RRT | Area (%) | RT | RRT | Area (%) |
| 2-Bromo-1-(4-fluorophenyl)-2-phenyl ethanone | 11.705 | 1.0 | 96.54 | 7.096 | 1.0 | 97.14 |
| 2-Bromo-1,2-diphenyl ethanone | 10.46 | 0.893 | nil | 6.576 | 0.927 | 0.25 |

EXAMPLE-5

4-Fluoro-α-[2-methyl-1-oxopropyl]-γ-oxo-N-β-diphenylbenzene butane amide

Acetone (320 ml) is taken in a 4 necked RB flask equipped with mechanical stirring rod, pressure equalization funnel and a $CaCl_2$ guard tube. 100 g (0.487 mol) of 4-methyl-3-oxo-N-phenyl pentanamide is added and stirred for 5 min to obtain clear solution. The solution is then cooled to 18.5±1.5° C., 80 g (0.578 mole) of potassium carbonate is introduced in one lot. A solution of 114 g (0.389 mol) of 2-Bromo-1-(4-fluorophenyl)-2-phenylethanone(as prepared in Example.4) in acetone (20 ml) is added to contents of flask in about 1½-2 hr period while maintaining the reaction temperature at 18.5±1.5° C. After addition the reaction mixture temperature is raised to 26±2° C. and maintained for additional 6 hours. The reaction mixture is filtered and the inorganics are washed with acetone (100 ml). The combined filtrate is concentrated to residual solid by removing acetone below 65° C. under vacuum. 32 ml of isopropyl alcohol is then added to the flask and solvent is removed completely under vacuum below 70° C. Again 32 ml of fresh isopropyl alcohol is added to residue and solvent is removed completely under vacuum below 70° C. 320 ml of isopropyl alcohol is added to the residual solid and the contents are heated to 82.5±2.5 and maintained at this temperature for 1 hour. The contents are gradually brought to 32±2.5° C. by cooling during a period of 1½-2 hours. The product is isolated on filter and washed with 32 ml of isopropyl alcohol and followed by water (200 ml). The material is dried at 75±5° C. in a vacuum oven, till water content of material is <0.5%. Yield 120 g (73.8%)

| | UPLC | | | HPLC | | |
|---|---|---|---|---|---|---|
| Peak | RT | RRT | Area (%) | RT | RRT | Area (%) |
| 4-Fluoro-α-[2-methyl-1-oxopropyl]-γ-oxo-N-β-diphenylbenzene butane amide | 13.25 | 1.0 | 99.62 | 25.112 | 1.0 | 99.62 |
| 1-(4-Fluorophenyl)-2-phenyl ethanone (II) | 8.063 | 0.608 | nil | 13.144 | 0.522 | nil |
| Desfluoro analog | 12.377 | 0.934 | 0.03 | 23.008 | 0.916 | 0.018 |
| Difluoro analog | 14.32 | 1.079 | nil | 27.501 | 1.093 | nil |
| Isomer | 12.93 | 0.980 | 0.01 | 22.40 | 0.960 | nil |
| Compound VIII | 14.38 | 1.085 | nil | 27.507 | 1.096 | nil |
| Compound VII | 18.65 | 1.407 | nil | 35.462 | 1.414 | nil |

EXAMPLE-6

4-Fluoro-α-[2-methyl-1-oxopropyl]-γ-oxo-N-β-diphenylbenzene butane amide

Acetone (120 ml) is taken in a 4 necked RB flask equipped with mechanical stirring rod, pressure equalization funnel and a CaCl$_2$ guard tube and is then cooled to 18.5±1.5° C. 40 g (0.0.29 mole) of potassium carbonate is introduced in one lot. A cold solution of 57 g (0.195 mol) of 2-Bromo-1-(4-fluorophenyl)-2-phenylethanone and 50 g (0.0.243 mol) of 4-methyl-3-oxo-N-phenyl pentanamide in acetone (120 ml) is added to the contents of flask in about 1½-2 hr period while maintaining the reaction temperature at 18.5±1.5° C. After addition the reaction mixture, the temperature is raised to 26±2° C. and maintained for additional 3 hours. The reaction mixture is filtered and the inorganics are washed with acetone (60 ml). The combined filtrate is concentrated to residual solid by removing acetone below 65° C. under vacuum. 40 ml of isopropyl alcohol is then added to the flask and solvent is removed completely under vacuum below 70° C. 180 ml of isopropyl alcohol is added to the residual solid and the contents are heated to 82.5±2.5 and maintained at this temperature for 1 hour. The contents are gradually brought to 32±2.5° C. by cooling during a period of 1½-2 hours. The product is isolated on filter and washed with 40 ml of isopropyl alcohol and followed by water (100 ml). The material is dried at 75±5° C. in a vacuum oven, till water content of material is <0.5%. Yield 63 g (77.7%).

| | UPLC | | | HPLC | | |
|---|---|---|---|---|---|---|
| Peak | RT | RRT | Area (%) | RT | RRT | Area (%) |
| 4-Fluoro-α-[2-methyl-1-oxopropyl]-γ-oxo-N-β-diphenylbenzene butane amide | 13.25 | 1.0 | 99.23 | 25.112 | 1.0 | 99.23 |
| 1-(4-Fluorophenyl)-2-phenyl ethanone (II) | 8.063 | 0.608 | nil | 13.144 | 0.522 | nil |
| Desfluoro analog | 12.377 | 0.934 | nil | 23.008 | 0.916 | 0.01 |
| Diflouro analog | 14.33 | 1.079 | nil | 27.503 | 1.092 | nil |
| Isomer | 12.90 | 0.980 | 0.04 | 22.40 | 0.960 | 0.033 |
| Compound VIII | 14.38 | 1.085 | nil | 27.507 | 1.096 | nil |
| Compound VII | 18.65 | 1.407 | nil | 35.462 | 1.414 | nil |

EXAMPLE-7

2-Chloro-1-(4-fluorophenyl)-2-phenylethanone

Sulfuryl chloride (66.6 g, 0.493 mol) is taken in a 4 necked RB flask equipped with mechanical strring rod, pressure equalization funnel and a CaCl$_2$ guard tube. The contents of the flask are cooled to 10-15° C. A solution of 1-(4-Fluorophenyl)-2-phenyl ethanone (100 g, 0.467 mol) in 150 ml of methylene chloride is added to the above flask in about 30-45 min while maintaining the temperature between 10-15° C. After completion of addition, the reaction mass is then stirred for additional 2½ hours at 15-20° C. TLC examination of reaction mixture showed the absence of starting material. The reaction mixture is slowly poured over crushed ice (600 g) and further diluted with methylene chloride (200 ml). The methylene chloride layer is separated and washed twice with 5% aqueous sodium bicarbonate (200 ml) followed by 5% aqueous sodium chloride(200 ml). The methylene chloride layer is dried over sodium sulphate. Methylene chloride is removed by distillation completely to obtain 2-Chloro-1-(4-fluorophenyl)-2-phenylethanone as a pale yellow liquid. Yield 114 g (98.6%)

| | UPLC | | | HPLC | | |
|---|---|---|---|---|---|---|
| Peak | RT | RRT | Area (%) | RT | RRT | Area (%) |
| 2-Chlor-1-(4-fluorophenyl)-2-phenyl ethanone | 10.497 | 1.0 | 96.85 | 5.885 | 1.0 | 97.44 |
| 2-Chloro-1,2-diphenyl ethanone | 9.26 | 0.881 | nil | 5.39 | 0.917 | Nil |
| 2,2-Dichloro-1(4-fluorophenyl)-2-phenyl ethanone | 15.771 | 1.362 | 2.79 | 9.035 | 1.537 | 1.75 |

EXAMPLE-8

4-Fluoro-α-[2-methyl-1-oxopropyl]-γ-oxo-N-β-diphenylbenzene butane amide

Acetone (100 ml) is taken in a 4 necked RB flask equipped with mechanical stirring rod, pressure equalization funnel and a CaCl$_2$ guard tube and is then cooled to about 25° C. 20 g (0.144 mole) of potassium carbonate is introduced in one lot, followed by 24.1 (0.097 mol) of 2-chloro1-(4-fluorophenyl)-2-phenylethanone and 23 g (0.111 mol) of 4-methyl-3-oxo-N-phenyl pentanamide are added to the contents of flask. The contents of the flask are raised 55-60° C. and maintained at reflux for additional 7-8 hours. The reaction mixture is filtered and the inorganics are washed with acetone (25 ml).The combined filtrate is concentrated to residual solid by removing acetone below 65° C. under vacuum. 25 ml of isopropyl alcohol is then added to the flask and solvent is removed completely under vacuum below 70° C. 90 ml of isopropyl alcohol is added to the residual solid and the contents are heated to 82.5±2.5 and maintained at this temperature for 1 hour. The contents are gradually brought to 32±2.5° C. by cooling during a period of 1½-2 hours. The product is isolated on filter and washed with 25 ml of isopropyl alcohol and followed by water (100 ml). The material is dried at 75±5° C. in a vacuum oven, till water content of material is <0.5%. Yield 30 g (74%)

| | UPLC | | | HPLC | | |
|---|---|---|---|---|---|---|
| Peak | RT | RRT | Area (%) | RT | RRT | Area (%) |
| 4-Fluoro-α-[2-methyl-1-oxopropyl]-γ-oxo-N-β-diphenylbenzene butane amide | 14.43 | 1.0 | 99.80 | 25.112 | 1.0 | 99.75 |
| 1-(4-Fluorophenyl)-2-phenyl ethanone (II) | 8.063 | 0.558 | nil | 13.144 | 0.522 | Nil |
| Desfluoro analog | 12.377 | 0.857 | nil | 23.008 | 0.916 | Nil |
| Difluoro analog | 15.62 | 1.03 | nil | 27.502 | 1.091 | Nil |
| Compound VIII | 15.65 | 1.08 | nil | 27.507 | 1.096 | Nil |
| Compound VII | 20.3 | 1.4 | nil | 35.462 | 1.414 | Nil |

EXAMPLE-9

4-Methyl-3-oxo-N-phenyl pentanamide

Methyl isobutyryl acetate (100 g, 0.693 mol) is placed in a 4 neck RB flask equipped with a stirring rod, thermometer socket and a distillation condenser. Aniline (71 g, 0.762 mol) and triethylamine (15 g, 0.148 mol) are added and the contents are heated to 80-85° C. under agitation. The contents are maintained at 80-85° C. for 1hr and the temperature is gradually raised to 120-125° C. The reaction is maintained for 4-6 hours, during which period methanol formed in the reaction is collected (48 ml). The reaction is continued till methanol no longer distills out the contents are cooled to 25-30° C. The reaction mixture is quenched with 2N hydrochloric acid (200 ml) and extracted with methylene chloride (100 ml). The aqueous layer is extracted twice with methylene chloride (2×100 ml). The combined methylene chloride extract (300 ml) is sequentially washed with 1N hydrochloric acid (50 ml), 5% aqueous sodium bicarbonate (50 ml) and 5% aq. sodium chloride (50 ml). The organic layer is concentrated to remove methylene chloride on a water bath at 50-55° C., traces of methlyene chloride are finally removed under vacuum. 4-Methyl-3-oxo-N-phenyl pentanamide (132 g, 92.7%, HPLC purity 98.85%) thus obtained is used in next step as such.

What is claimed is:

1. A process for controlling impurities during preparation of a compound of formula (I)

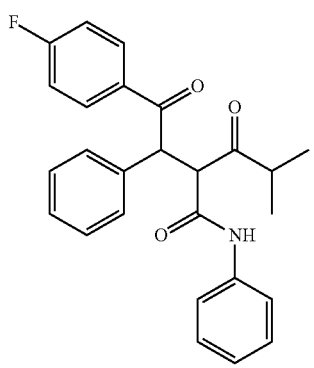

Formula (I)

the processing comprising:
performing a Friedel-Crafts condensation of fluorobenzene with phenylacetyl chloride at a reaction temperature ranging from about—10° C. to 0° C. to afford a compound of Formula II;

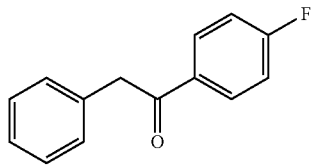

Formula II performing a halogenation of said formula II in at least one inert solvent to afford a compound of formula III wherein X is halogen;

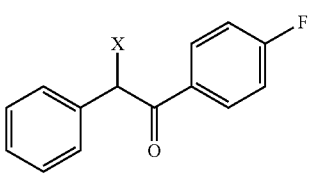

Formula III and
performing a nucleophilic substitution of said formula III in a base in a solvent having a compound of formula IV to afford the compound of formula I;

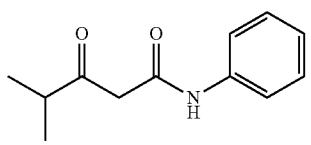

Formula IV wherein said impurities consist of α-[-methyl-1-oxopropyl]-γ-oxo-N-β-diphenylbenzene butan amide, 3,4-difluoro-α-[2-methyl-1-oxopropyl]-γ-oxo-n-β-diphenylbenzene butane amide, 1,4-bis(4-fluorophenyl)-2,3-diphenylbutane-1,4-dione, 2{-2[-(4-fluorophenyl)-2-oxo-1-phenylethyl)]}-4-methyl-3-oxo pentanoate and 1-(4-fluorophenyl)-2-phenyl ethanone.

2. The process of claim 1, wherein said Friedel-Crafts condensation is carried out in presence of Lewis acid catalyst to afford said Formula II.

3. The process of claim 2, wherein said lewis acid catalyst is selected from the group comprising FeCl3, SbCl5, BF3, TiCl4, ZnC2 or AlCl3.

4. The process of claim 1, wherein the halogenation of said formula II is carried out in situ in presence of methylene chloride.

5. The process of claim 1, wherein said halogen is selected from the group consisting of bromine and chlorine.

6. The process of claim 1, wherein said base for nucleophilic substitution of said formula III is either sodium carbonate, potassium carbonate cesium carbonate, triethyl amine, or diisopropylethylamine.

7. The process of claim 1, wherein said solvent for nucleophilic substitution of said formula III is selected from the group consisting of tetrahydrofuran, 1,2-dimethoxy ethane, methylene chloride, ethyl acetate, acetone, methyl ethyl ketone, methyl isobutyl ketone, isopropanol, acetonitrile, dimethyl formamide, N-methyl pyyrolidinone, dimethyl sulfoxide, methanol or a mixture there of.

8. The process of claim 7, wherein said solvent is acetone.

9. The process of claim 1, wherein said formula I contains less than 0.05% of said α-[2-methyl-1-oxopropyl]-γ-oxo-N-β-diphenylbenzene butane amide.

10. The process of claim 1, wherein said formula I is completely devoid of said 3,4-difluoro-α-[2-methyl-1-oxopropyl]-γ-oxo-n-β-diphenylbenzene butane amide.

11. The process of claim 1, wherein said formula I is completely devoid of said methyl, 2{-2[-4-fluorophenyl)-2-oxo-1-phenylethyl)]}-4-methyl-3-oxo pentanoate.

12. The process of claim 1, wherein said formula I is completely devoid of said 1-(4-fluorophenyl)-2-phenyl ethanone.

13. The process of claim 1, wherein presence of the impurity in the preparation of formula I is being determined by ultra performance liquid chromatography (UPLC).

\* \* \* \* \*